United States Patent [19]
Allen, Jr. et al.

[11] 3,936,464
[45] Feb. 3, 1976

[54] 1-ACYL-3-[2-(4-PHENYL-1-PIPERIDINYL)ETHYL]INDOLINES

[75] Inventors: George Rodger Allen, Jr., Old Tappan, N.J.; Francis Joseph McEvoy, Pearl River, N.Y.

[73] Assignee: American Cyanamid Company, Stamford, Conn.

[22] Filed: Oct. 25, 1974

[21] Appl. No.: 518,023

[52] U.S. Cl. 260/293.61; 260/295 B; 260/326.11 R; 424/263; 424/267
[51] Int. Cl.² .................................... C07D 401/06
[58] Field of Search ............... 260/293.61, 295 B

[56] References Cited
UNITED STATES PATENTS

| | | | |
|---|---|---|---|
| 3,527,761 | 9/1970 | Archibald et al. | 260/293 |
| 3,564,009 | 2/1971 | Yamamoto et al. | 260/326.16 |
| 3,639,414 | 2/1972 | Archer | 260/295 B |
| 3,655,674 | 4/1972 | Archibald | 260/293.61 |

*Primary Examiner*—G. Thomas Todd
*Attorney, Agent, or Firm*—Edward A. Conroy, Jr.

[57] ABSTRACT

This disclosure describes new substituted 1-acyl-3-[2-(4-phenyl-1-piperidinyl)ethyl]indolines which possess hypotensive activity.

10 Claims, No Drawings

1-ACYL-3-[2-(4-PHENYL-1-PIPERIDINYL)ETHYL-]INDOLINES

BRIEF SUMMARY OF THE INVENTION

This invention relates to novel substituted 1-acyl-3-[2-(4-phenyl-1-piperidinyl)ethyl]indolines and to methods for the preparation of these compounds. The novel substituted 1-acyl-3-[2-(4-phenyl-1-piperidinyl)ethyl]indolines of the present invention may be represented by the following general formula:

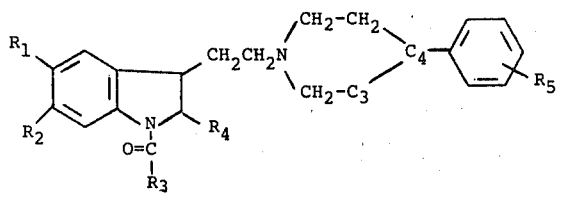

wherein $R_1$ is hydrogen or a lower alkoxy group having up to 4 carbon atoms; $R_2$ is hydrogen and $R_1$ and $R_2$ taken together is methylenedioxy; $R_3$ is a lower alkyl group having up to 4 carbon atoms; $R_4$ is hydrogen or a lower alkyl group having up to 4 carbon atoms; $R_5$ is hydrogen, chloro or trifluoromethyl; and the moiety $-C_3-C_4-$ is a trivalent radical of the formulae:

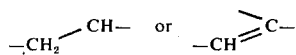

The substituted 1-acyl-3-[2-(4-phenyl-1-piperidinyl)-ethyl]indolines of the present invention are obtainable as crystalline materials having characteristic melting points and absorption spectra. They are appreciably soluble in many organic solvents such as lower alkanols, acetone, ethyl acetate, and the like but are generally insoluble in water. These compounds are organic bases and thus are capable of forming acid-addition salts with a variety of organic and inorganic salt-forming reagents. Thus, acid-addition salts, formed by admixture of the organic free base with one equivalent of an acid in a neutral solvent, are formed with such acids as sulfuric, phosphoric, hydrochloric, hydrobromic, sulfamic, citric, maleic, fumaric, tartaric, acetic, benzoic, gluconic, ascorbic, and related acids. The acid addition salts are, in general, crystalline solids relatively soluble in water, methanol and ethanol but are relatively insoluble in non-polar organic solvents such as diethyl ether, benzene, toluene and the like. For purposes of this invention, the free bases are equivalent to their non-toxic acid-addition salts.

The compounds of the present invention may be prepared as illustrated in the following reaction scheme:

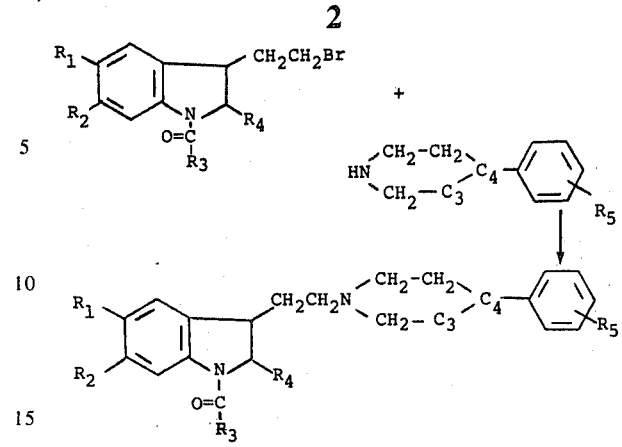

wherein $R_1$, $R_2$, $R_3$, $R_4$, $R_5$ and the moiety $-C_3-C_4-$ are as defined hereinbefore. This reaction is preferably conducted in an inert solvent such as benzene, toluene, xylene, dioxane and the like at temperatures of 50°–140°C. although temperatures of 100°–110°C. are preferable. The preparation of the starting 3-(2-bromoethyl)indolines is described in U.S. Pat. No. 3,751,416.

The novel compounds of the present invention have hypotensive activity which was demonstrated in the following test procedure. Conscious male albino Sherman strain rats averaging approximately 250 grams in weight were fastened to rat boards in a supine position by means of canvas vests and limb ties. The femoral areas were anesthetized (subcutaneous infiltration of lidocaine), and the left or right common iliac arteries were exposed and clamped off proximally by an artery clamp and distally with thread. Incisions were made near the tie and short nylon catheters were inserted and tied in place. The other end of the catheters were fitted with 24 gauge hubless needles attached to thick-walled polyethylene tubes. The test compounds were administered to the animals orally by gavage (stomach tube). The test compounds were ordinarily suspended or dissolved in 2 percent aqueous starch solution, one milliliter of which gave, per 100 grams of body weight, the desired dose. Mean arterial blood pressure was measured 4 hours after administration of the compounds. Comparisons were then made to the mean control pressure of 122 mm. of mercury which is the average of a number of controls recorded over months of testing. Blood pressure measurements were made with four Statham P23 Db strain gauges (Statham Instruments, Inc., Los Angeles, Calif.), attached to a Sanborn Polyviso Recorder equipped with four strain gauge preamplifiers with averaging circuits for measuring mean arterial pressure.

Table I below summarizes the activity of typical compounds of the present invention.

Table I

| Compound | No. of Rats | Median Arterial Blood Pressure (mm. of Hg) |
|---|---|---|
| 1-Acetyl-3-[2-(3,6-dihydro-4-phenyl-1(2H)-pyridyl)ethyl]indoline | 3 | 92 |
| 1-Acetyl-3-[2-(4-phenylpiperidino)-ethyl]-indoline | 3 | 87 |
| 1-Acetyl-3-{2-[4-(p-chlorophenyl)-3,6-dihydro-1(2H)-pyridyl]ethyl}indoline | 3 | 93 |
| 5-Acetyl-7-[2-(3,6-dihydro-4-phenyl-1(2H)-pyridyl)ethyl]-6,7-dihydro-5H-1,3-dioxolo-[4,5-f]indole | 2 | 80 |
| 1-Acetyl-3-[2-(3,6-dihydro-4-phenyl-1(2H)-pyridyl)ethyl-5-methoxy-2-methylindoline | 2 | 90 |
| 5-Acetyl-6,7-dihydro-7-[2-(4-phenylpiperidino)-ethyl]-5H-1,3-dioxolo-[4,5-f]indole | 3 | 95 |

Table I -continued

| Compound | No. of Rats | Median Arterial Blood Pressure (mm. of Hg) |
|---|---|---|
| 1-Acetyl-5-methoxy-2-methyl-3-[2-(4-phenyl-piperidino)ethyl]indoline | 2 | 87 |
| 1-Acetyl-3-{2-[3,6-dihydro-($\alpha,\alpha,\alpha$-trifluoro-p-tolyl)-1(2H)-pyridyl]ethyl}indoline | 3 | 98 |
| 1-Acetyl-3-{2-[4-($\alpha,\alpha,\alpha$-trifluoro-p-tolyl)-piperidino]ethyl}indoline | 3 | 96 |

The invention will be described in greater detail in conjunction with the following specific examples.

EXAMPLE 1

Preparation of 5-acetyl-6,7-dihydro-7-[2-(4-phenylpiperidino)-ethyl]-5H-1,3-dioxolo[4,5-f]indole A solution of 580 mg. (18.6 mmol) of 5-acetyl-6,7-dihydro-7-(2-bromoethyl)-5H-1,3-dioxolo[4,5-f]indole and 600 mg. (37.2 mmol) of 4-phenylpiperidine in 30 ml. of toluene is heated at reflux temperature for 18 hours. The solvent is removed, and the residue is extracted with diethyl ether (2 × 25 ml.), and the solid is removed by filtration. The filtrate is evaporated to give a residue that crystallizes on trituration with petroleum ether. The material is recrystallized from dilute acetone to give crystals, m.p. 101°–103°C.

EXAMPLE 2

Preparation of 1-benzyl-4-hydroxy-4-($\alpha,\alpha,\alpha$-trifluoro-p-tolyl)-piperidine A solution of 22.5 g. (0.1 mol) of p-bromobenzotrifluoride in 50 ml. of ether is stirred under argon at ice-bath temperature while 50 ml. of 2M butyl lithium solution is added dropwise. The solution is then stirred at room temperature for 15 minutes, and then cooled again to 0°C. A solution of 17.7 g. of N-benzylpiperidone in 50 ml. of ether is then added over 30 minutes and the reaction is stirred at room temperature for 3 hours. The solution is poured into cracked ice-water and filtered to remove some solid. The filtrate is diluted with methylene chloride, and the organic layer is dried and evaporated. The residue is triturated with petroleum ether (b.p. 30°–60°C.), and the solid is collected, washed with ether and dried to give white solid, m.p. 115°–117°C.

EXAMPLE 3

Preparation of 4-hydroxy-4-($\alpha,\alpha,\alpha$-trifluoro-p-tolyl)piperidine

A mixture of 10.0 g. (0.03 mol) of 1-benzyl-4-hydroxy-4-($\alpha,\alpha,\alpha$-trifluoro-p-tolyl)piperidine and 1.0 g. of 10% Pd/C in 100 ml. of ethanol containing 2.0 ml. of acetic acid is shaken under hydrogen. The mixture is filtered and the filtrate is evaporated to give a white solid which is dissolved in 50 ml. of water and rendered alkaline by addition of 1N NaOH solution. Filtration gives white crystals, m.p. 136°–138°C.

EXAMPLE 4

Preparation of 1,2,3,6-tetrahydro-4-($\alpha,\alpha,\alpha$-trifluoro-p-tolyl)-pyridine hydrochloride A solution of 4.9 g. of 4-hydroxy-4-($\alpha,\alpha,\alpha$-trifluoro-p-tolyl)piperidine in 33 ml. of 37% hydrochloric acid solution and 66 ml. of acetic acid is stirred at reflux temperature for 18 hours. The solution is evaporated and the residue is triturated with acetone to give white crystals, m.p. 213°–215°C.

EXAMPLE 5

Preparation of 1-acetyl-3-[2-(3,6-dihydro-4-phenyl-1(2H)-pyridyl)ethyl]indoline

A mixture of 2.68 g. of 1-acetyl-3-(2-bromoethyl)-indoline, 2.00 g. of 4-phenyl-1,2,3,6-tetrahydropyridine hydrochloride and 4.00 g. of sodium bicarbonate in 40 ml. of sec-butyl alcohol is stirred at reflux temperature for 18 hours. The cooled mixture is filtered, and the filtrate is evaporated. The residue is dissolved in acetone and the addition of water gives white crystals, m.p. 109°–111°C.

EXAMPLE 6

Preparation of 1-acetyl-3-[2-(4-phenylpiperidino)ethyl]indoline

In the manner described in Example 1, reaction of 1-acetyl-3-(2-bromoethyl)indoline with 4-phenyl-piperidine gives a solid that is recrystallized from dilute ethanol to give white crystals, m.p. 92°–93°C.

EXAMPLE 7

Preparation of 1-acetyl-3-{2-[4-(p-chlorophenyl)-3,6-dihydro-1(2H)-pyridyl]ethyl}indoline In the manner described in Example 1, reaction of 1-acetyl-3-(2-bromoethyl)indoline with 4-(p-chlorophenyl)-1,2,3,6-tetrahydropyridine gives white crystals, m.p. 116°–118°C., after recrystallization from dilute methanol.

EXAMPLE 8

Preparation of 5-acetyl-7-[2-(3,6-dihydro-4-phenyl-1(2H)-pyridyl)ethyl]-6,7-dihydro-5H-1,3-dioxolo[4,5-f]indole In the manner described in Example 1, treatment of 5-acetyl-7-(2-bromoethyl)-6,7-dihydro-5H-1,3-dioxolo[4,5-f]-indole with 1,2,3,6-tetrahydro-4-phenylpyridine gives white crystals, m.p. 90°–91°C., after recrystallization from dilute acetone.

EXAMPLE 9

Preparation of 1-acetyl-3-[2-(3,6-dihydro-4-phenyl-1(2H)-pyridyl)ethyl]-5-methoxy-2-methylindoline In the manner described in Example 1, treatment of 1-acetyl-3-(2-bromoethyl)-5-methoxy-2-methylindoline with 1,2,3,6-tetrahydro-4-phenylpyridine gives white crystals, m.p. 113°–115°C., after recrystallization from dilute methanol.

EXAMPLE 10

Preparation of
1-acetyl-3-[2-(4-ethyl-4-phenylpiperidino)ethyl]-indoline

In the manner described in Example 1, treatment of 1-acetyl-3-(2-bromoethyl)indoline with 4-ethyl-4-phenylpiperidine gives an oil. On reaction with molar equivalent of fumaric acid, a crystalline fumarate results. After recrystallization from acetone-hexane it melts at 173°–178°C.

EXAMPLE 11

Preparation of
1-acetyl-5-methoxy-2-methyl-3-[2-(4-phenylpiperidino)ethyl]indoline In the manner described in Example 1, treatment of 1-acetyl-3-(2-bromoethyl)-5-methoxy-2-methylindoline with 4-phenylpiperidine gives the product as an amorphous solid.

EXAMPLE 12

Preparation of
1-acetyl-3-{-2-[4-hydroxy-4-($\alpha,\alpha,\alpha$-trifluoro-p-tolyl)-piperidino]ethyl}indoline In the manner described in Example 5, reaction of 1-acetyl-3-(2-bromoethyl)indoline with 4-hydroxy-4-($\alpha,\alpha,\alpha$-trifluoro-p-tolyl)piperidine gives white crystals, which melt at 141°–143°C., after recrystallization from dilute acetone.

EXAMPLE 13

Preparation of
1-acetyl-3-{2-[3,6-dihydro-($\alpha,\alpha,\alpha$-trifluoro-p-tolyl)-1(2H)-pyridyl]ethyl}indoline In the manner described in Example 5, treatment of 1-acetyl-3-(2-bromoethyl)indoline with 1,2,3,6-tetrahydro-4-($\alpha,\alpha,\alpha$-trifluoro-p-tolyl)pyridine gives crystals, m.p. 85°–88°C., after recrystallization from dilute acetone.

EXAMPLE 14

Preparation of
1-acetyl-3-{2-[4-($\alpha,\alpha,\alpha$-trifluoro-p-tolyl)piperidino]ethyl}indoline A mixture of 2.07 g. (5 mmol) of 1-acetyl-3{2-[3,6-dihydro-($\alpha,\alpha,\alpha$-trifluoro-p-tolyl)-1(2H)-pyridyl]ethyl}indoline, 200 ml. of platinum oxide and 50 ml. of ethanol is shaken under hydrogen. The mixture is filtered and the filtrate is evaporated. The residue is triturated with petroleum ether (b.p. 30°–60°C.) to give a solid that is recrystallized from dilute acetone to give crystals, m.p. 98°–100°C.

EXAMPLE 15

In the manner described in Example 1, reaction of 5-propionyl-6-methyl-6,7-dihydro-7-(2-bromoethyl)-5H-1,3-dioxolo[4,5-f]indole with 4-phenylpiperidine, 4-(p-chlorophenyl)piperidine, or 1,2,3,6-tetrahydro-4-($\alpha,\alpha,\alpha$-trifluoro-p-tolyl)pyridine provides the corresponding 5-propionyl-6-methyl-6,7-dihydro-7-[2-(4-phenylpiperidino) ethyl]-5H-1,3-dioxolo[4,5-f]indole, 5-propionyl-6-methyl-6,7-dihydro-7-{2-[4(p-chlorophenyl)piperidino]ethyl}-5H-1,3-dioxolo-[4,5-f]-indole, and 5-propionyl-6-methyl-6,7-dihydro-7-{2-[3,6-dihydro-($\alpha,\alpha,\alpha$-trifluoro-p-tolyl)-1(2H)-pyridyl]ethyl}-5H-1,3-dioxolo[4,5-f]indole.

EXAMPLE 16

In the manner described in Example 5, reaction of 1-isobutyryl-2-ethyl-3-(2-bromoethyl)-5-ethoxyindoline with 4-phenyl-1,2,3,6-tetrahydropyridine, 4-(p-chlorophenyl)-1,2,3,6-tetrahydropyridine, or 4-(p-trifluoromethylphenyl)piperidine provides the corresponding 1-isobutyryl-2-ethyl-5-ethoxy-3-[2-(4-phenyl-3,6-dihydro-1(2H)-pyridyl)ethyl]indoline, 1-isobutyryl-2-ethyl-5-ethoxy-3-{2-[4-(p-chlorophenyl)-3,6-dihydro-1(2H)-pyridyl]ethyl}indoline, and 1-isobutyryl-2-ethyl-5-ethoxy-3-{2-[4-(p-trifluoromethylphenyl)piperidino]-ethyl}indoline.

EXAMPLE 17

In the manner described in Example 14, reduction of 1-isobutyryl-2-ethyl-5-ethoxy-3-[2-(4-phenyl-3,6-dihydro-1(2H)-pyridyl)ethyl]indoline and 1-isobutyryl-2-ethyl-5-ethoxy-3-{2-[4-(p-chlorophenyl)-3,6-dihydro-1(2H)-pyridyl]-ethyl} indoline provides the corresponding 1-isobutyryl-2-ethyl-5-ethoxy-3-[2-(4-phenylpiperidino)ethyl]indoline and 1-isobutyryl-2-ethyl-5-ethoxy-3-{2-[4-(p-chlorophenyl)-piperidino]ethyl} indoline.

We claim:
1. A compound selected from the group consisting of those of the formulae:

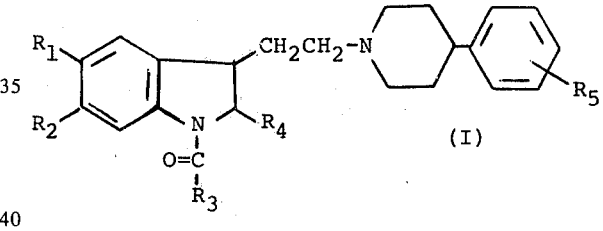

(I)

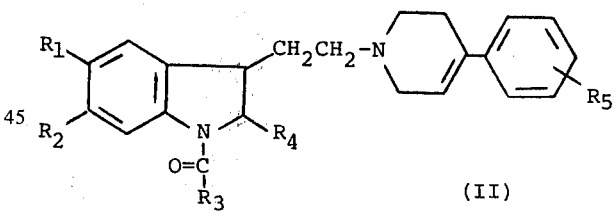

(II)

wherein $R_1$ is hydrogen or a lower alkoxy group, $R_2$ is hydrogen and $R_1$ and $R_2$ taken together is methylenedioxy, $R_3$ is a lower alkyl group, $R_4$ is hydrogen or a lower alkyl group, and $R_5$ is hydrogen, chloro or trifluoromethyl; and the pharmacologically acceptable acid-addition salts thereof.

2. The compound according to claim 1, formula (II) thereof, wherein $R_1$ is hydrogen, $R_2$ is hydrogen, $R_3$ is methyl, $R_4$ is hydrogen, and $R_5$ is hydrogen; 1-acetyl-3-[2-(3,6-dihydro-4-phenyl-1(2H)-pyridyl)ethyl]indoline.

3. The compound according to claim 1, formula (I) thereof, wherein $R_1$ is hydrogen, $R_2$ is hydrogen, $R_3$ is methyl, $R_4$ is hydrogen, and $R_5$ is hydrogen; 1-acetyl-3-[2-(4-phenylpiperidino)ethyl]indoline.

4. The compound according to claim 1, formula (II) thereof, wherein $R_1$ is hydrogen, $R_2$ is hydrogen, $R_3$ is methyl, $R_4$ is hydrogen, and $R_5$ is para-chloro; 1-acetyl-3-{2-[4-(p-chlorophenyl)-3,6-dihydro-1(2H)-pyridyl]ethyl}indoline.

5. The compound according to claim 1, formula (II) thereof, wherein $R_1$ and $R_2$ taken together is methylenedioxy, $R_3$ is methyl, $R_4$ is hydrogen, and $R_5$ is hydrogen; 5-acetyl-7-[2-(3,6-dihydro-4-phenyl-1(2H)-pyridyl)ethyl]-6,7-dihydro-5H-1,3-dioxolo[4,5-f]indole.

6. The compound according to claim 1, formula (II) thereof, wherein $R_1$ is methoxy, $R_2$ is hydrogen, $R_3$ is methyl, $R_4$ is methyl, and $R_5$ is hydrogen; 1-acetyl-3-[2-(3,6-dihydro-4-phenyl-1(2H)-pyridyl)ethyl]-5-methoxy-2-methylindoline.

7. The compound according to claim 1, formula (I) thereof, wherein $R_1$ and $R_2$ taken together is methylenedioxy, $R_3$ is methyl, $R_4$ is hydrogen, and $R_5$ is hydrogen; 5-acetyl-6,7-dihydro-7-[2-(4-phenylpiperidino)ethyl]-5H-1,3-dioxolo-[4,5-f]indole.

8. The compound according to claim 1, formula (I) thereof, wherein $R_1$ is methoxy, $R_2$ is hydrogen, $R_3$ is methyl, $R_4$ is methyl, and $R_5$ is hydrogen; 1-acetyl-5-methoxy-2-methyl-3-[2-(4-phenyl-1-piperidno)ethyl]indoline.

9. The compound according to claim 1, formula (II) thereof, wherein $R_1$ is hydrogen, $R_2$ is hydrogen, $R_3$ is methyl, $R_4$ is hydrogen, and $R_5$ is para-trifluoromethyl; 1-acetyl-3-{2-[3,6-dihydro-($\alpha,\alpha,\alpha$-trifluoro-p-tolyl)-1(2H)-pyridyl]-ethyl}indoline.

10. The compound according to claim 1, formula (I) thereof, wherein $R_1$ is hydrogen, $R_2$ is hydrogen, $R_3$ is methyl, $R_4$ is hydrogen, and $R_5$ is para-trifluoromethyl; 1-acetyl-3{2-[4-($\alpha,\alpha,\alpha$-trifluoro-p-tolyl)piperidino]ethyl}indoline.

\* \* \* \* \*